(12) United States Patent
Kamiya et al.

(10) Patent No.: US 8,787,528 B2
(45) Date of Patent: Jul. 22, 2014

(54) DIAGNOSTIC DEVICE SYSTEM

(75) Inventors: Takeshi Kamiya, Kanagawa (JP);
Yusuke Kitagawa, Kanagawa (JP);
Yasunori Ohta, Kanagawa (JP);
Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 393 days.

(21) Appl. No.: 13/067,362

(22) Filed: May 26, 2011

(65) Prior Publication Data
US 2011/0291610 A1    Dec. 1, 2011

(30) Foreign Application Priority Data

May 27, 2010   (JP) .................................. 2010-121860

(51) Int. Cl.
*H05G 1/06*     (2006.01)
*H05G 1/10*     (2006.01)
*H05G 1/64*     (2006.01)
*H01L 27/146*   (2006.01)

(52) U.S. Cl.
USPC ............ 378/102; 378/91; 378/98.8; 378/103; 378/194

(58) Field of Classification Search
CPC ............. H05G 1/06; H05G 1/10; H05G 1/64; H01L 27/146
USPC .................... 378/91, 98, 98.8, 101–103, 189, 378/193–198, 204, 210
See application file for complete search history.

(56) References Cited

U.S. PATENT DOCUMENTS

| | | | | |
|---|---|---|---|---|
| 5,077,771 A | * | 12/1991 | Skillicorn et al. | 378/102 |
| 5,749,057 A | * | 5/1998  | Takagi           | 455/569.2 |
| 6,169,384 B1 | * | 1/2001 | Shannon          | 320/107 |

(Continued)

FOREIGN PATENT DOCUMENTS

| | | |
|---|---|---|
| CN | 2862470 Y    | 1/2007 |
| JP | 2001154120 A | 6/2001 |

(Continued)

OTHER PUBLICATIONS

Notice of Reasons for Rejection, issued by the Japanese Patent Office (JPO) on Oct. 15, 2013 in connection with Japanese Patent Application No. 2010-121860.

(Continued)

*Primary Examiner* — Anastasia Midkiff
(74) *Attorney, Agent, or Firm* — Jean C. Edwards, Esq.; Edwards Neils PLLC

(57) ABSTRACT

A diagnostic device system has a weight-reduced rechargeable battery. When a portable radiographic apparatus and a portable X-ray source are carried to and used for imaging at a private home or a care home, the portable radiographic apparatus and the portable X-ray source are loaded on an automobile. When the charge amount of rechargeable batteries for operation housed in the portable radiographic apparatus or the portable X-ray source loaded on the automobile is low, or when there are plural destinations and the charge amount of the rechargeable batteries becomes low, a rechargeable battery for charging mounted on the automobile is used to charge the rechargeable batteries for operation while traveling. Because the rechargeable batteries for operation are charged while traveling, a large number of rechargeable batteries for operation does not need to be charged in advance, whereby the weight of the rechargeable batteries for operation can be reduced.

7 Claims, 9 Drawing Sheets

(56) References Cited

U.S. PATENT DOCUMENTS

| | | | |
|---|---|---|---|
| 6,169,782 B1 * | 1/2001 | Zetterlund | 378/103 |
| 6,982,132 B1 * | 1/2006 | Goldner et al. | 429/162 |
| 7,359,482 B2 * | 4/2008 | Schmitt | 378/98.8 |
| 2005/0276379 A1 | 12/2005 | Polichar et al. | |
| 2006/0017028 A1 | 1/2006 | Ohara et al. | |
| 2008/0240358 A1 * | 10/2008 | Utschig et al. | 378/107 |
| 2009/0028295 A1 | 1/2009 | Ohta et al. | |
| 2009/0140177 A1 * | 6/2009 | Whittum et al. | 250/493.1 |
| 2009/0202899 A1 * | 8/2009 | Pyszczek | 429/152 |

FOREIGN PATENT DOCUMENTS

| | | |
|---|---|---|
| JP | 2006-208303 | 8/2006 |
| JP | 2010005219 A | 1/2010 |
| WO | WO-2006008979 A1 | 1/2006 |

OTHER PUBLICATIONS

Chinese Office Action issued by the State Intellectual Property Office (SIPO) on May 7, 2014, in Chinese Patent Application No. 201110137627.8.

* cited by examiner

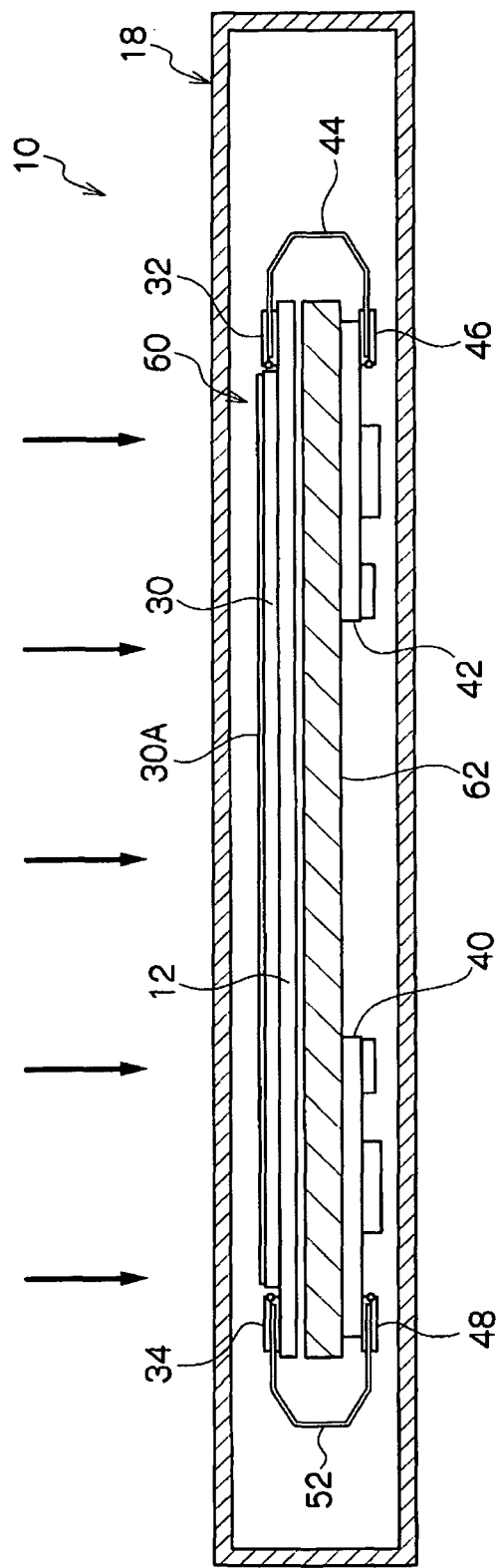

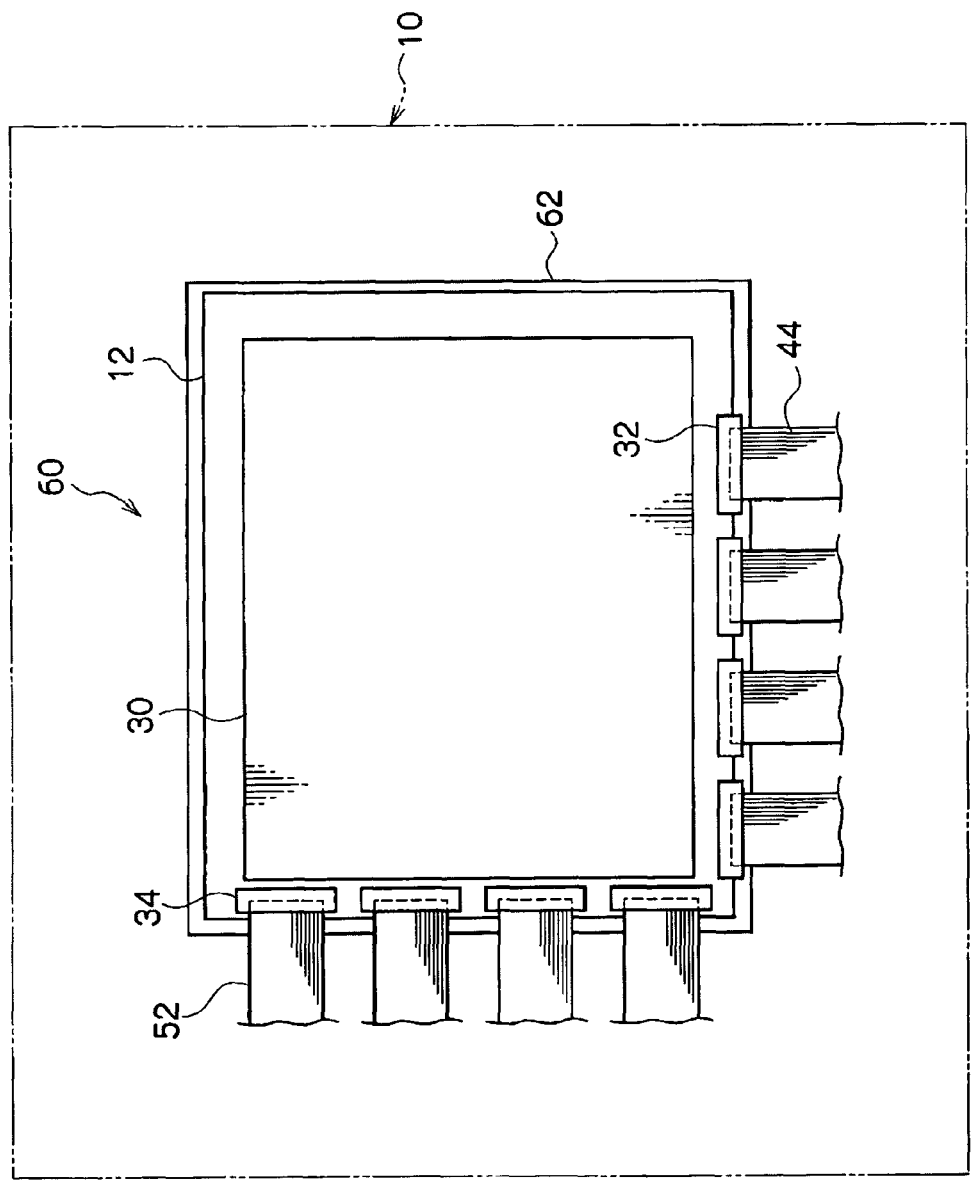

DIAGNOSTIC DEVICE SYSTEM

CROSS-REFERENCE TO RELATED APPLICATION

This application claims priority under 35 USC 119 from Japanese Patent Application No. 2010-121860 filed on May 27, 2010, the disclosure of which is incorporated by reference herein.

BACKGROUND

1. Technical Field

The present invention relates to a diagnostic device system used for diagnosis of diseases of humans or animals.

2. Related Art

A radiological image detector (diagnostic device) described in Japanese Patent Application Laid-Open (JP-A) No. 2006-208303 is mounted with a rechargeable battery. The radiological image detector is configured to operate with electric power of the battery.

However, in the conventional art, for example, when a diagnostic device is used in visiting a personal home or visiting a care home, the charge amount of the rechargeable battery used in the diagnostic device decreases in a case that there are plural destinations, and the diagnostic device cannot be used in the destinations. Thus, the charge amount of the rechargeable battery needs to be increased and the weight of the conventional rechargeable battery has been heavy.

SUMMARY

It is an object of the invention to reduce the weight of the rechargeable battery.

A diagnostic device system according to a first aspect of the invention comprises: a diagnostic device that is supplied with electric power for operation and is used for diagnosing diseases of humans or animals; and a rechargeable battery for operation that is charged by a rechargeable battery for charging, wherein the rechargeable battery for charging is mounted on a vehicle and the rechargeable battery for operation supplies electric power to the diagnostic device to operate the diagnostic device.

In accordance with the above-described structure, the diagnostic device which operates by obtaining electric power from the rechargeable battery for operation is used for diagnosis of diseases of humans or animals. The rechargeable battery of operation is charged by the rechargeable battery of charging mounted on a vehicle.

In this way, the rechargeable battery for charging mounted on the vehicle charges the rechargeable battery for operation which supplies electric power to the diagnostic device so that the rechargeable battery for operation is charged in a moving vehicle when the diagnostic device is used in visiting a personal home or visiting a care home, for example.

Due thereto, the rechargeable battery for operation does not need to be charged in large quantity in advance; therefore, the weight of the rechargeable battery for operation can be reduced.

A diagnostic device system according to a second aspect of the invention is the diagnostic device system of the first aspect, wherein the diagnostic device is at least one of a portable radiographic apparatus for recording a radiological image expressed by irradiated radiation or a portable X-ray source for irradiating radiation on the portable radiographic apparatus.

In accordance with the above-described structure, the diagnostic device is at least one of the portable radiographic apparatus for recording a radiographic image expressed by an irradiated radiation and the portable X-ray source for irradiating a radiation on the portable radiographic apparatus.

The weight of the rechargeable battery for operation which operates the portable radiographic apparatus and the portable X-ray source is reduced so that a load on a subject can be reduced in a case where the subject is imaged while holding the portable radiographic apparatus during the imaging at a visited place, for example.

A diagnostic device system according to a third aspect of the invention is the diagnostic device system of the first aspect or the second aspect, wherein the vehicle on which the rechargeable battery for charging is mounted is an automobile and the rechargeable battery for charging is used to realize the functions of the automobile.

In accordance with the above-described the structure, the rechargeable battery for charging is mounted on an automobile as a vehicle and is used to realize the functions of the automobile. Due thereto, the rechargeable battery for charging does not need to be provided as a dedicated component only for charging the rechargeable battery for operation, and the rechargeable battery of operation can be charged in a low-cost structure.

A diagnostic device system according to a fourth aspect of the invention is any diagnostic device system of the first to the third aspects, wherein the capacity of the rechargeable battery for operation is smaller than the capacity of the rechargeable battery for charging.

In accordance with the above-described structure, the capacity of the rechargeable battery for operation is set to be smaller than the capacity of the rechargeable battery for charging. Thereby, the rechargeable battery for charging can charge the rechargeable battery for operation in a stable state.

A diagnostic device system according to a fifth aspect of the invention is any diagnostic device system of the first to the forth aspects, wherein the rechargeable battery for operation has a larger self-discharging rate than the rechargeable battery for charging.

In accordance with the above-described structure, the rechargeable battery for operation is further increased in the self-discharging rate than the rechargeable battery for charging. Due thereto, the rechargeable battery for charging can effectively charge the rechargeable battery for operation.

A diagnostic device system according to a sixth aspect of the invention is any diagnostic device system of the first to the fifth aspects, wherein the rechargeable battery for operation is attachable to and detachable from the diagnostic device.

In accordance with the above-described the structure, the rechargeable battery for operation is attachable/detachable to the diagnostic device. When there occurs a trouble that the rechargeable battery for charging cannot charge, the rechargeable battery for operation mounted on the diagnostic device is exchanged with a preliminary rechargeable battery for operation, thereby the diagnostic device is operated.

A diagnostic device system according to a seventh aspect of the invention is any diagnostic device system of the first to the fifth aspects comprising an accommodating unit that houses the rechargeable battery for operation therein and comprises an electric cable for supplying electric power from the housed rechargeable battery for operation to the diagnostic device.

In accordance with the above-described structure, the diagnostic device is connected to the rechargeable battery for operation via the electric cable of the accommodating unit. For example, when plural diagnostic devices are used, the plural diagnostic devices are connected to one rechargeable battery for operation via the electric cables, thereby the plural diagnostic devices are operated.

According to the invention, the weight of the battery can be reduced.

BRIEF DESCRIPTION OF THE DRAWINGS

Exemplary embodiments of the present invention will be described in detail based on the following figures, wherein:

FIG. 6 is a cross-sectional view showing the portable radiographic apparatus used in the diagnostic device system according to the first exemplary embodiment of the invention;

FIG. 7 is a plan view showing the portable radiographic apparatus used in the diagnostic device system according to the first exemplary embodiment of the invention;

DETAILED DESCRIPTION

One example of a diagnostic device system 64 according to a first exemplary embodiment of the invention will be described with reference to FIG. 1A, FIG. 1B to FIG. 7. The arrow UP in the Figures indicates the upward direction.

(Entire Structure)

Figure 1A:
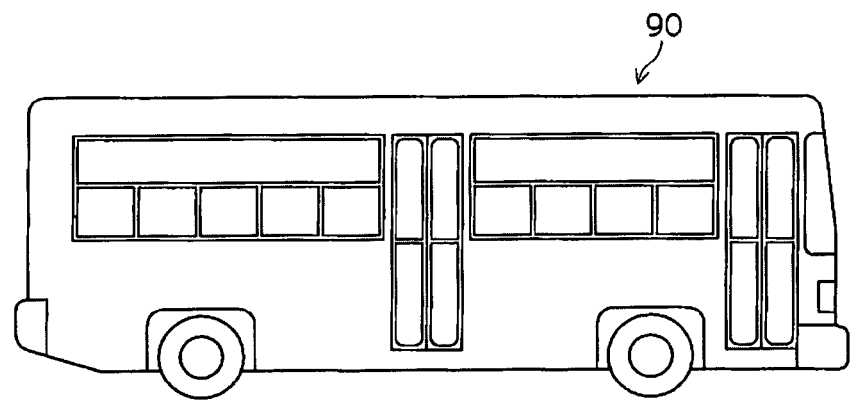
FIG. 1A is a structural diagram showing an automobile according to a first exemplary embodiment of the invention.
Figure 1B:
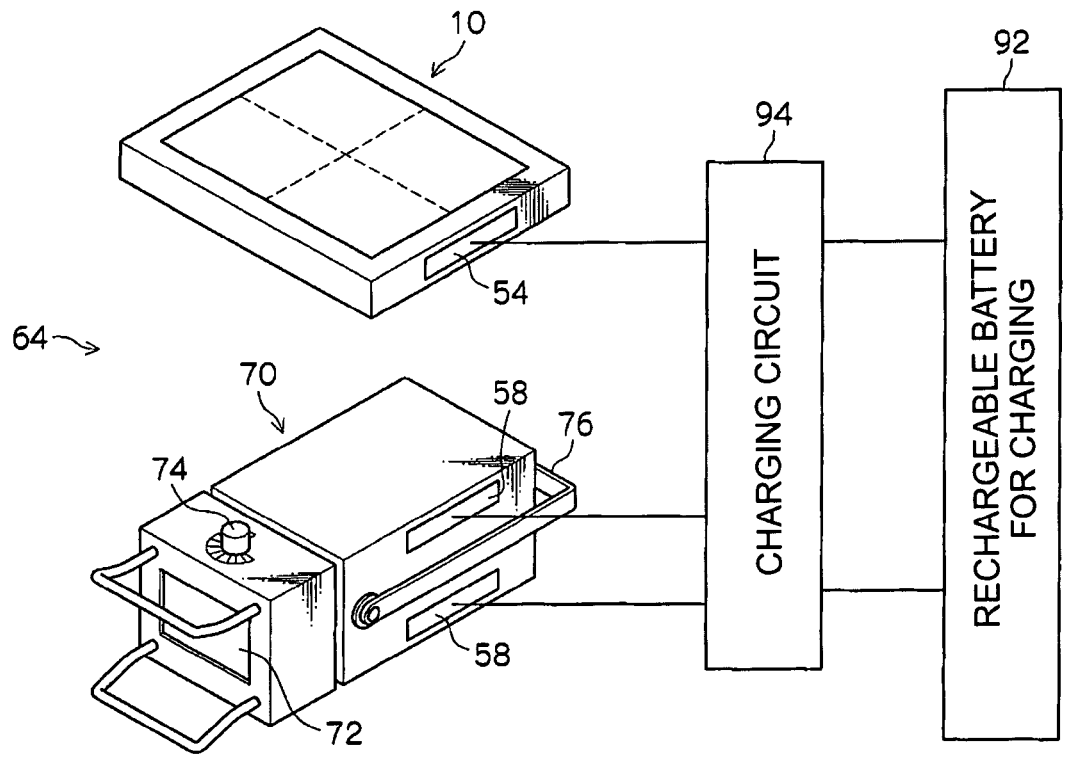
FIG. 1B is a structural diagram showing a diagnostic device system and a rechargeable battery for charging according to the first exemplary embodiment of the invention.
Figure 5:
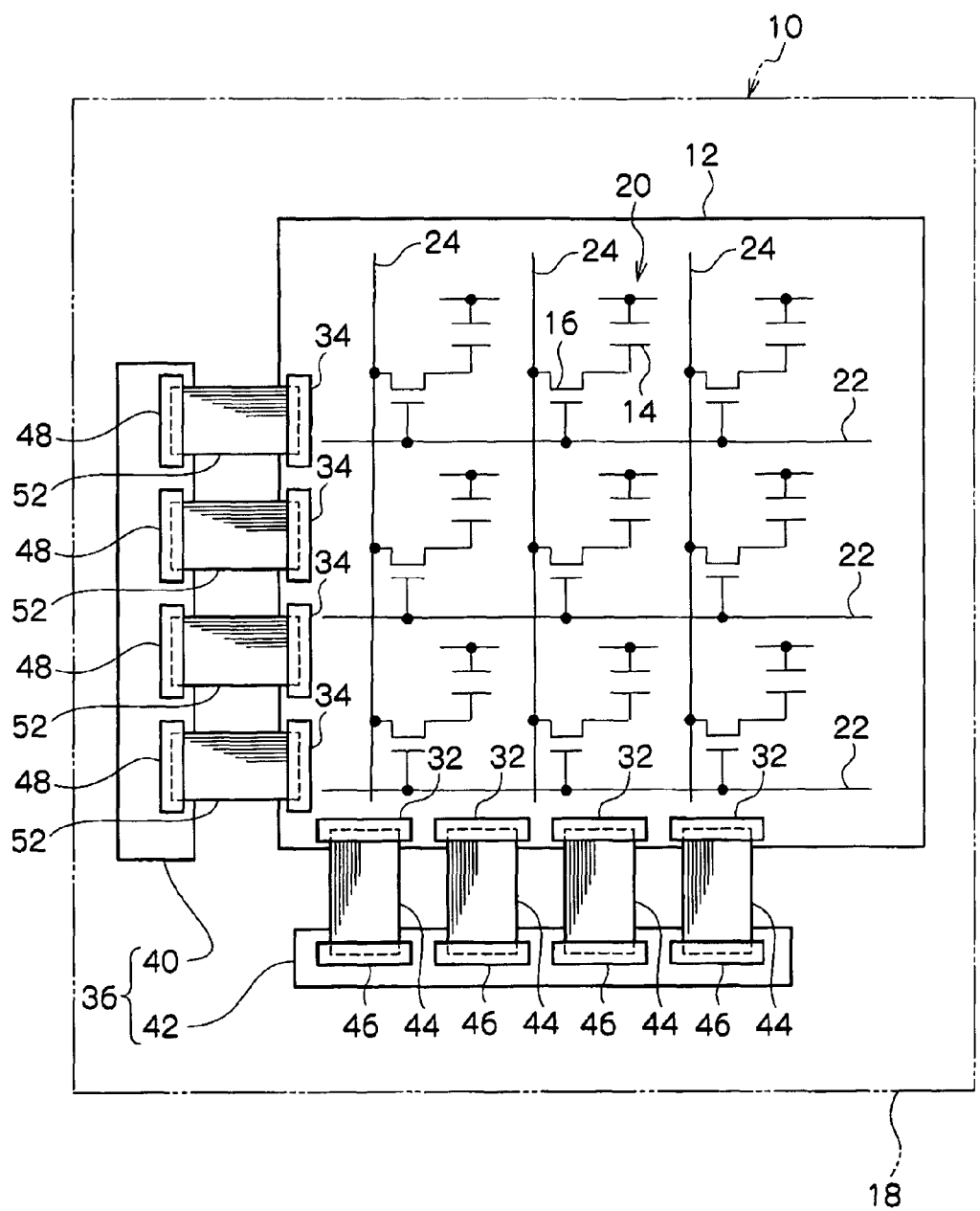
FIG. 5 is a circuit diagram showing the portable radiographic apparatus used in the diagnostic device system according to the first exemplary embodiment of the invention.

As shown in FIG. 5, a radiographic element 12 is provided inside a housing 18 of a portable radiographic apparatus 10 (so-called cassette) as one exemplary diagnostic device provided in the diagnostic device system 64 (see FIG. 1B). The radiographic element 12 includes an upper electrode, a semiconductor layer, and a lower electrode, and is provided with, in a two-dimensional shape, plural pixels 20 each including a sensor portion 14 for receiving light and accumulating charges and a TFT switch 16 for reading out the charges accumulated in the sensor portion 14.

The radiographic element 12 is provided with plural scan wirings 22 for powering on or off the TFT switches 16 and plural signal wirings 24 for reading out the charges accumulated in the sensor portions 14 in a mutually intersecting manner.

The radiographic element 12 according to the exemplary embodiment is attached at its surface with a scintillator 30 (see FIG. 6 and FIG. 7) made of GOS or CsI. The scintillator 30 includes a light shield 30A (see FIG. 6) for shielding generated light, at the opposite surface to the attached radiographic element 12 in order to prevent the generated light from leaking to the outside.

In the radiographic element 12, a radiation such as irradiated X-ray is converted into light by the scintillator 30, and the light is irradiated on the sensor portions 14. The sensor portion 14 is configured to receive the light irradiated from the scintillator 30 and accumulate charges.

Further, due to any of the TFT switches 16 connected to the signal wirings 24 being powered on, an electric signal (image signal) indicating a radiological image in accordance with the charge amount accumulated in the sensor portion 14, flows through each signal wiring 24.

Connectors 32 for connection are arranged so as to be lined-up at one end side, in the signal wiring direction, of the radiographic element 12. Connectors 34 are arranged so as to be lined-up at one end side in the scan wiring direction. Each signal wiring 24 is connected to the connector 32 and each scan wiring 22 is connected to the connector 34.

In the exemplary embodiment, there is provided a controlling portion 36 for controlling the radiation detection by the radiographic element 12 and controlling the signal processing on the electric signal flowing through each signal wiring 24, and the controlling portion 36 includes a signal detecting circuit 42 and a scan signal controlling circuit 40.

The signal detecting circuit 42 is provided with plural connectors 46 and the connectors 46 are electrically connected to one ends of flexible cables 44. The flexible cables 44 are connected at the other ends to the connectors 32 and each incorporate an amplifying circuit for amplifying an inputted electric signal for each signal wiring 24. With the structure, due to the electric signal inputted from each signal wiring 24 being amplified by the amplifying circuit and detected, the signal detecting circuit 42 detects the charge amount accumulated in each sensor portion 14, as information of each pixel 20 constituting an image.

On the other hand, the scan signal controlling circuit 40 is provided with connectors 48 and the connectors 48 are electrically connected to one ends of flexible cables 52. The other ends of the flexible cables 52 are connected to the connectors 34 and the scan signal controlling circuit 40 is configured to output a control signal for powering on or off the TFT switch 16 to each scan wiring 22.

As shown in FIG. 6, the portable radiographic apparatus 10 according to the exemplary embodiment includes an imaging portion 60 for imaging a radiological image expressed by an irradiated radiation. In the imaging unit 60, the radiographic element 12 is arranged on one surface of a support substrate 62 formed in a plate shape (see FIG. 5), and the signal detecting circuit 42 and the scan signal controlling circuit 40 corresponding to the radiographic element 12 are arranged on the other surface of the support substrate 62.

Figure 3:
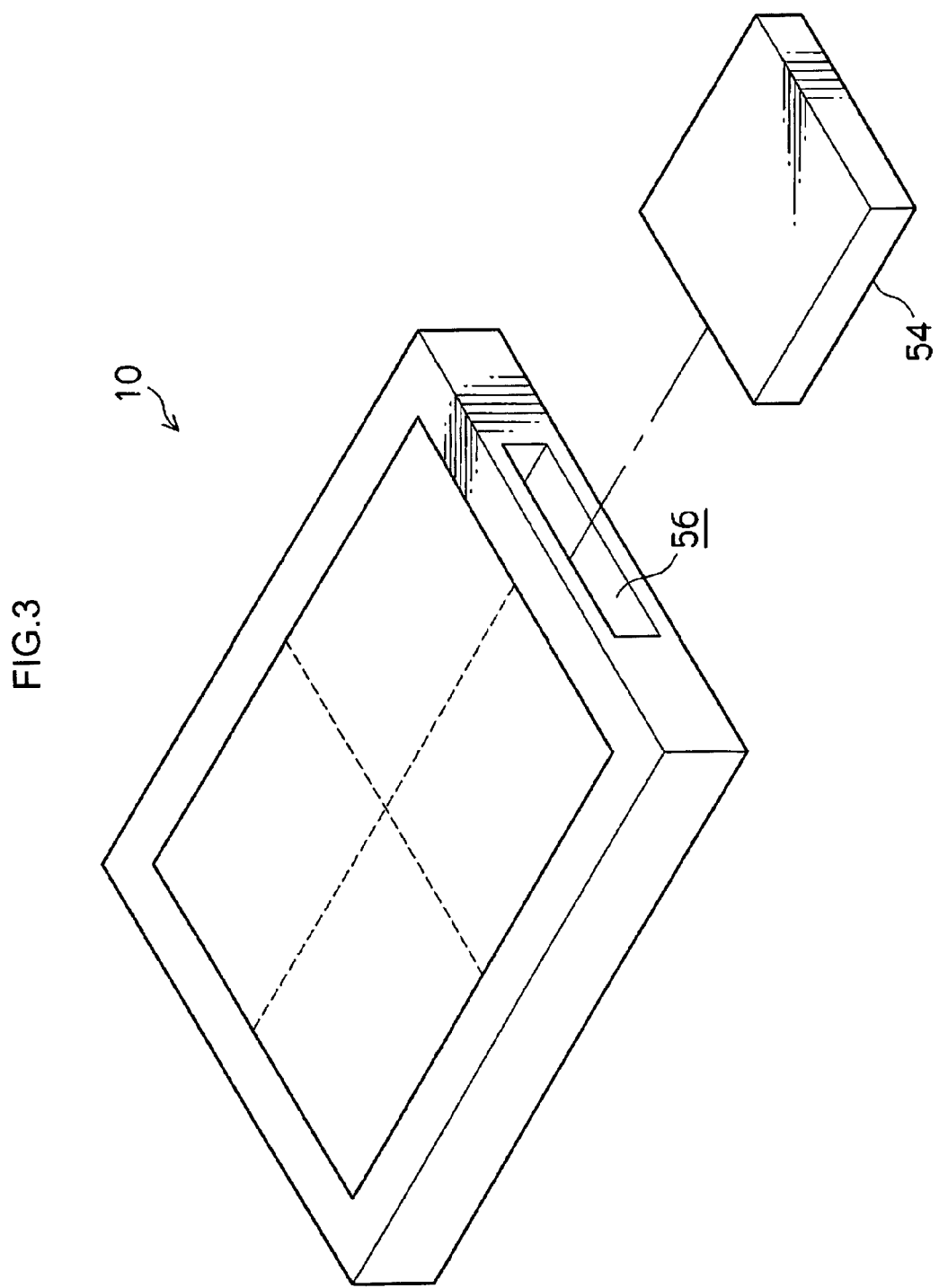
FIG. 3 is a perspective view showing a portable radiographic apparatus used in the diagnostic device system according to the first exemplary embodiment of the invention.

As shown in FIG. 3, the portable radiographic apparatus 10 is provided with an rechargeable battery for operation 54 which operates the portable radiographic apparatus 10 and the rechargeable battery for operation 54 is attachable/detachable to an accommodating portion 56 provided on a side surface of the portable radiographic apparatus 10.

Figure 4:
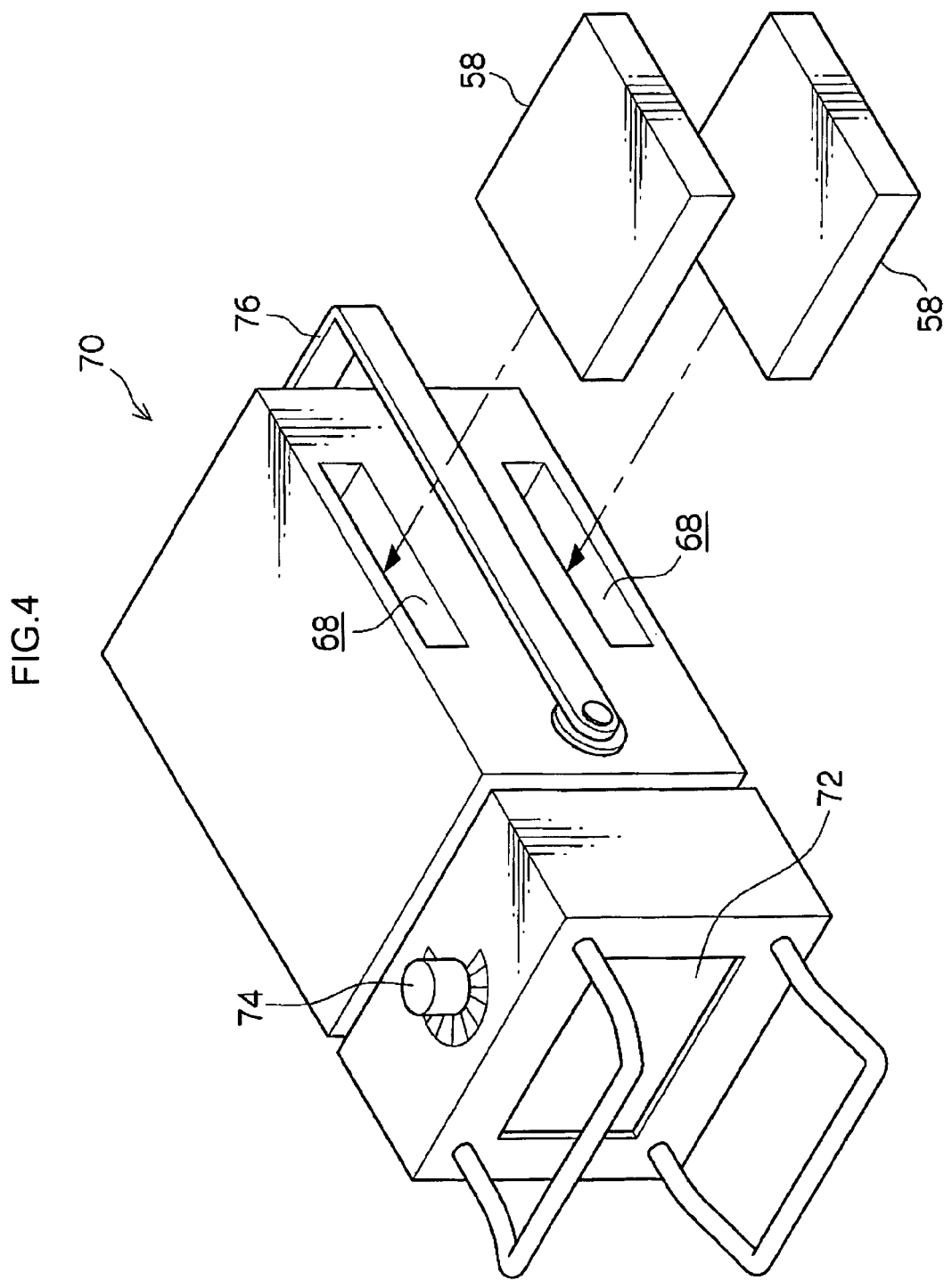
FIG. 4 is a perspective view showing a portable X-ray source used in the diagnostic device system according to the first exemplary embodiment of the invention.

In contrast, as shown in FIG. 4, a portable X-ray source 70 for irradiating a radiation on the portable radiographic apparatus 10 is provided with an irradiating window 72 for irradiating an X-ray, an adjustment dial 74 for adjusting a collimator of the portable X-ray source 70, and a gripping portion 76 to be gripped for carrying the portable X-ray source 70.

The portable X-ray source 70 is provided with two rechargeable batteries 58 for operation which operates the portable X-ray source 70. The portable X-ray source 70 is provided in its side surface with two accommodating portions 68 for accommodating the rechargeable batteries for operation 58, and the rechargeable batteries for operation 58 are attachable/detachable to the accommodating portions 68. The rechargeable batteries for operation 54, 58 and the method for charging the rechargeable batteries for operation 54, 58 will be described below in detail.

The operations of the portable radiographic apparatus 10 and the portable X-ray source 70 according to the exemplary embodiment will be described below.

Figure 2:
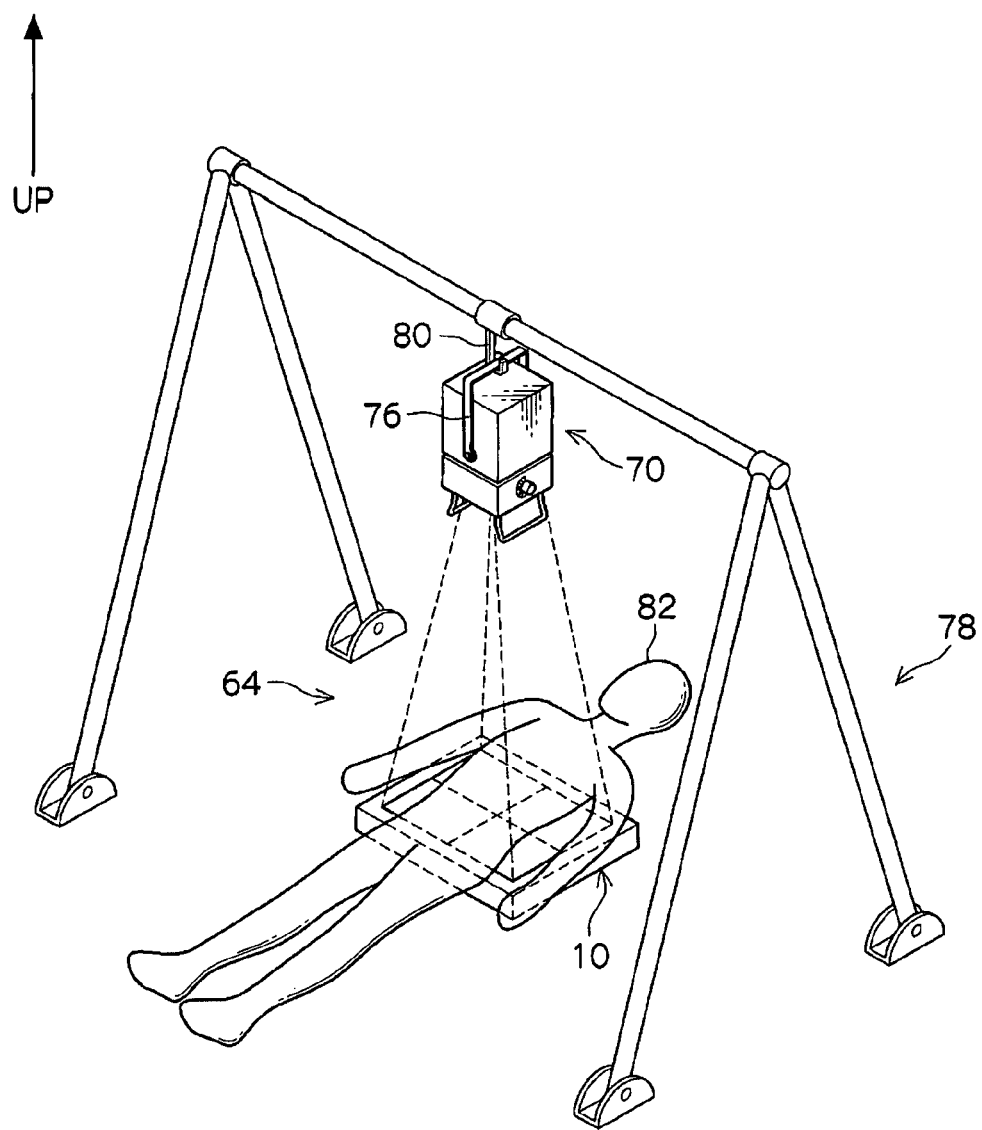
FIG. 2 is a perspective view showing the diagnostic device system according to the first exemplary embodiment of the invention.

As shown in FIG. 2, the portable radiographic apparatus 10 and the portable X-ray source 70 are mounted on an automobile 90 (see FIG. 1A) described later to be carried to a personal home or a care home. The portable radiographic apparatus 10 is arranged apart from the portable X-ray source 70 for generating a radiation during the imaging of a radiological image. More specifically, the gripping portion 76 of the portable X-ray source 70 is hooked on a hooking portion 80 of an angle 78 which is easily assembled at a personal home or care home so that the portable radiographic apparatus 10 and the portable X-ray source 70 are arranged apart from each other in the vertical direction.

An imaging position where a subject 82 is positioned is between the portable X-ray source 70 and the portable radiographic apparatus 10, and when the imaging of a radiological image is instructed, the portable X-ray source 70 irradiates a radiation having the radiation amount corresponding to previously-given imaging conditions. Due to the radiation, that is emitted from the portable X-ray source 70, passing through the subject 82 at the imaging position, the radiation carries image information, and thereafter, is irradiated on the portable radiographic apparatus 10.

As shown in FIG. 6, in the radiographic element 12, a radiation such as irradiated X-ray is converted into a light by the scintillator 30, and the light is irradiated on the sensor portions 14 (see FIG. 5). The sensor portions 14 receive the light irradiated from the scintillator 30, and accumulate the charges.

As shown in FIG. 5, during the image reading, ON signals (+10 to 20V) are sequentially applied from the scan signal controlling circuit 40 to gate electrodes of the TFT switches 16 of the radiographic element 12 via the scan wirings 22. Due thereto, the TFT switches 16 of the radiographic element 12 are sequentially powered on so that electric signals corresponding to the amounts of charges accumulated in the sensor portions 14 start to flow to the signal wirings 24. The signal detecting circuit 42 detects the amount of charges accumulated in each sensor portion 14 based on the electric signal flowed to the signal wiring 24 of the radiographic element 12 as the information of each pixel 20 constituting the image. Due thereto, the image information, that expresses the image expressed by the radiation irradiated on the radiographic element 12, is obtained.

(Structures of Essential Parts)

The rechargeable batteries for operation 54, 58 and the method for operating the rechargeable batteries 54, 58 for operation will be described below.

The rechargeable battery for operation 54 has the same shape and the same characteristics as the rechargeable battery for operation 58 and the rechargeable battery for operation 54 is exchangeable with the rechargeable battery for operation 58.

As described above, as shown in FIG. 3, the portable radiographic apparatus 10 is provided with one accommodating portion 56 for accommodating the rechargeable battery for operation 54. In contrast, as shown in FIG. 4, the portable X-ray source 70 is provided with two accommodating portions 68 for accommodating the rechargeable batteries for operation 58.

The number of accommodating portions 56 and the number of accommodating portions 68 are determined based on electric power consumptions of the portable radiographic apparatus 10 and the portable X-ray source 70 per unit number of images while the radiological images are recorded. More specifically, in designing the portable radiographic apparatus 10 and the portable X-ray source 70, the power consumptions per unit number of images while the radiological images are recorded are measured with respect to each of the portable radiographic apparatus 10 and the portable X-ray source 70, so that the numbers of accommodating portions 56, 68 are obtained to meet the following formula and thereby to provide the accommodating portions 56, 68.

(Electric power consumption per unit number of images of the portable radiographic apparatus 10)/(Electric power consumption per unit number of images of the portable X-ray source 70)=(The number of accommodating portions 56)/(The number of accommodating portions 68).

The electric power consumptions for plural subjects are measured in consideration of a difference between the electric power consumptions per unit number of images of the portable radiographic apparatus 10 and the portable X-ray source 70, and a representative value is appropriately selected from the plural measurement values. For example, the electric power consumption as the representative value can be appropriately selected from the following values.

1. A value obtained by adding a margin (about 10%) to the maximum electric power consumption (this value is considered to be the best for preventing the rechargeable battery for operation from running out of power)
2. A value of the maximum electric power consumption
3. 3σ (σ is a standard deviation)
4. An average value
5. A mode value On the other hand, as shown in FIGS. 1A and 1B, a rechargeable battery 92 for charging, that charges the rechargeable batteries for operation 54, 58 is provided and the rechargeable battery for charging 92 is mounted on the automobile 90. The automobile 90 is a gasoline-powered car travelling with gasoline, and the rechargeable battery for charging 92 is an electric power source for supplying electric power to electric components (such as headlight) of the automobile 90.

More specifically, the automobile 90 is provided with a charging circuit 94 for enabling the rechargeable batteries for operation 54, 58 to be charged by the rechargeable battery for charging 92. For example, when the portable radiographic apparatus 10 and the portable X-ray source 70 are used in visiting a personal home or visiting a care home, the rechargeable batteries for operation 54, 58 can be charged by the rechargeable battery for charging 92 via the charging circuit 94 in the travelling automobile 90.

The capacities of the rechargeable batteries for operation 54, 58 are set to be smaller than the capacity of the rechargeable battery for charging 92. The rechargeable batteries for operation 54, 58 are set to be larger in the self-discharging rate than the rechargeable battery for charging 92. That is, the rechargeable battery for charging 92 is more difficult to discharge than the rechargeable batteries 54, 58.

The methods for calculating and measuring the self-discharging rate will be described below.

Self-discharging rate of battery[%]=(Initial discharge capacity−discharge capacity after storage)/Initial discharge capacity×100

<Measuring Method>

First stage: Charge a single battery or assembled battery at an ambient temperature of 20±5° C. in a method designated by the manufacturer.

Second stage: Discharge the single battery or assembled battery at the ambient temperature of 20±5° C. at a constant current of 0.2 $I_t$[A] until the battery voltage reaches the predefined discharge-terminating voltage. The discharge amount at this time is assumed as the initial discharge capacity. $I_t$[A] is an hourly-rate current of the signal battery or assembled battery.

Third stage: Charge the single battery or assembled battery at the ambient temperature of 20±5° C. in a method designated by the manufacturer.

Fourth stage: Leave the single battery or assembled battery at the ambient temperature of 20±5° C. for 28 days.

Fifth stage: Discharge the single battery or assembled battery at the ambient temperature 20±5° C. at the constant current of 0.2 $I_t$[A] until the battery voltage reaches the predefined discharge-terminating voltage. The discharge amount at this time is assumed as the discharge capacity after storage.

(Operations/Effects)

The operations and effects of the diagnostic device system 64 will be described below.

As shown in FIG. 1A and FIG. 1B, the portable radiographic apparatus 10 and the portable X-ray source 70 are loaded on the automobile 90 for carrying the portable radiographic apparatus 10 and the portable X-ray source 70 to a destination and using the same for imaging at a personal home or a care home.

When the charge amounts of the rechargeable batteries for operation 54, 58 housed in the portable radiographic apparatus 10 or the portable X-ray source 70 loaded on the automobile 90 are low or when the charge amounts of the batteries 54, 58 become low on the way of plural destinations, the rechargeable battery for charging 92 mounted on the automobile 90 is used to charge the rechargeable batteries for operation 54, 58 during travelling.

In this way, the rechargeable batteries for operation 54, 58 are charged during the travelling so that the rechargeable batteries for operation do not need to be charged in large quantity in advance. Thus, the weights of the rechargeable batteries for operation 54, 58 can be reduced.

The weights of the rechargeable batteries for operation 54, 58 are reduced so that the weights of the portable radiographic apparatus 10 and the portable X-ray source 70 in which the rechargeable batteries for operation 54, 58 are housed can be reduced.

The portable radiographic apparatus 10 is reduced in its weight so that a load to a subject can be reduced when the subject is imaged while holding the portable radiographic apparatus 10 at a visited place, for example.

Since the rechargeable batteries for operation 54, 58 can be charged during the travelling, the capacities of the rechargeable batteries for operation 54, 58 can be determined based on the number of images to be captured (imaging order) at one visit.

The rechargeable battery for charging 92 is mounted on the automobile 90 and is used to realize the functions of the automobile 90. Thus, the rechargeable battery for charging 92 does not need to be provided as a dedicated component only for charging the rechargeable batteries for operation 54, 58, thereby charging the rechargeable batteries for operation 54, 58 in a low-cost structure.

The capacities of the rechargeable batteries for operation 54, 58 are set to be smaller than the capacity of the rechargeable battery for charging 92. Thus, the rechargeable battery for charging 92 can charge the rechargeable batteries for operation 54, 58 in a stable state.

The rechargeable batteries for operation 54, 58 are set to be larger in the self-discharging rate than the rechargeable battery for charging 92. That is, the rechargeable battery for charging 92 is more difficult to discharge than the rechargeable batteries for operation 54, 58. Thus, the rechargeable batteries for operation 54, 58 can be effectively charged when the rechargeable battery for charging 92 is used to charge the rechargeable batteries for operation 54, 58.

The rechargeable batteries for operation 54, 58 are attachable/detachable to the portable radiographic apparatus 10 and the portable X-ray source 70. When there occurs a trouble that the rechargeable battery for charging 92 cannot charge, the rechargeable batteries for operation 54, 58 mounted on the portable radiographic apparatus 10 and the portable X-ray source 70 are exchangeable with the preliminary rechargeable batteries for operation 54, 58, thereby operating the portable radiographic apparatus 10 and the portable X-ray source 70.

The invention has been described in detail for the specific exemplary embodiment, but the invention is not limited to the exemplary embodiment and it is clear to those skilled in the art that other various exemplary embodiments are possible within the scope of the invention. For example, the portable radiographic apparatus 10 and the portable X-ray source 70 are described as the devices constituting the diagnostic device system 64 but either one of them may be used.

In the above exemplary embodiment, the portable radiographic apparatus 10 and the portable X-ray source 70 are described as the devices constituting the diagnostic device system 64 but the devices are not particularly limited to the portable radiographic apparatus 10 and the portable X-ray source 70 and an ultrasonic diagnostic device or electrocardiographic testing device may be used.

In the above exemplary embodiment, the rechargeable battery for charging 92 used for the automobile 90 (gasoline-powered car) travelling with gasoline is described, but the invention is not limited thereto, and a rechargeable battery used for diesel-powered car, hybrid car or electric car may be used as the rechargeable battery for charging.

In the above exemplary embodiment, there is described with reference to the Figures how the rechargeable batteries for operation 54, 58 are charged by the rechargeable battery for charging 92 while being mounted on the portable radiographic apparatus 10 and the portable X-ray source 70, but the invention is not limited thereto, and the rechargeable batteries for operation 54, 58 removed from the portable radiographic apparatus 10 and the portable X-ray source 70 may be charged by the rechargeable battery for charging 92.

In the above exemplary embodiment, though not particularly stated, when the portable radiographic apparatus 10 and the portable X-ray source 70 are used to image the subject 82, a notebook-type personal computer for controlling the portable radiographic apparatus 10 and the portable X-ray source 70 may be used. The personal computer may be operated by the rechargeable batteries for operation 54, 58.

One example of a diagnostic device system 100 according to a second exemplary embodiment of the invention will be described below with reference to FIG. 8A, FIG. 8B and FIG.

9. The same members as those in the first exemplary embodiment are denoted with the same reference numerals and an explanation thereof will be omitted.

Figure 8A:
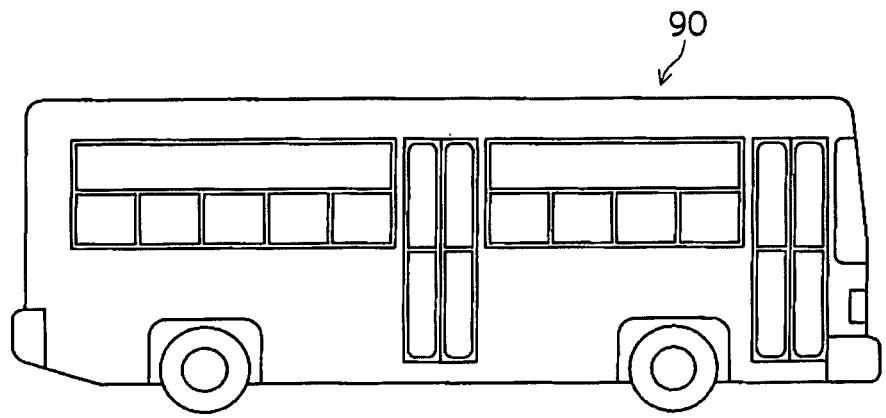
FIG. 8A is a structure diagram showing an automobile according to a second exemplary embodiment of the invention.
Figure 8B:
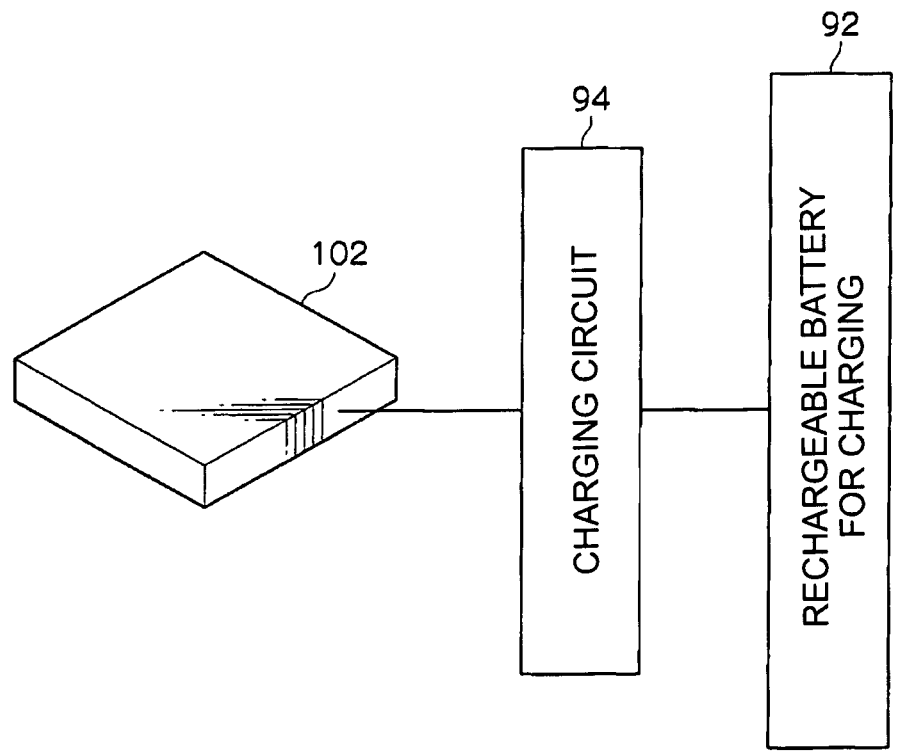
FIG. 8B is a structure diagram showing a diagnostic device system and a rechargeable battery for charging according to the second exemplary embodiment of the invention.

As shown in FIG. 8A and FIG. 8B, an rechargeable battery for operation 102 for operating the portable radiographic apparatus 10 and the portable X-ray source 70 is directly charged from the rechargeable battery for charging 92 via the charging circuit 94.

Figure 9:
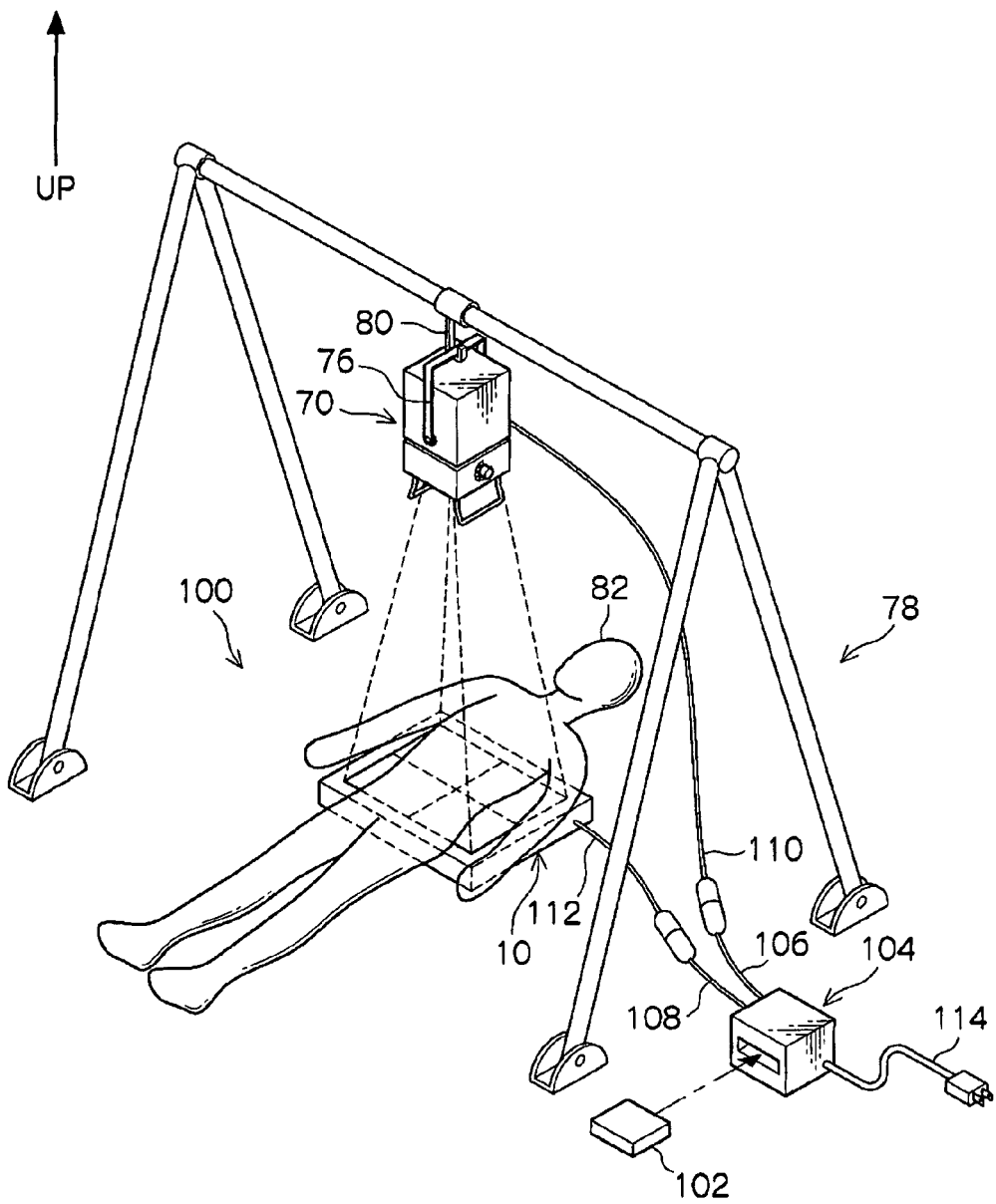
FIG. 9 is a perspective view showing the diagnostic device system according to the second exemplary embodiment of the invention.

As shown in FIG. 9, a accommodating unit 104 for accommodating the rechargeable battery for operation 102 therein is provided. When the portable radiographic apparatus 10 and the portable X-ray source 70 are powered at a visited place, the rechargeable battery for operation 102 is housed in the accommodating unit 104. Electric cables 106, 108 provided in the accommodating unit 104 are connected to electric cables 110, 112 extending from the portable radiographic apparatus 10 and the portable X-ray source 70. Thus, the rechargeable battery for operation 102 supplies electric power to the portable radiographic apparatus 10 and the portable X-ray source 70 via the accommodating unit 104.

The accommodating unit 104 is provided with a power supply cable 114, and the power supply cable 114 is connected to an outlet (such as wall outlet) capable of supplying electric power so that the rechargeable battery for operation 102 housed in the accommodating unit 104 is charged via a charging circuit (not shown) provided in the accommodating unit 104.

That is, the rechargeable battery for operation 102 is chargeable from the rechargeable battery for charging 92 while moving to a destination, and is housed in the accommodating unit 104 to be connected to an outlet via the power supply cable 114 for charging at the visited place.

As described above, the rechargeable battery for operation 102 housed in the accommodating unit 104 supplies electric power to the portable radiographic apparatus 10 and the portable X-ray source 70 via the electric cables 106, 108 at a visited place. Thus, one rechargeable battery for operation 102 can be used to operate the portable radiographic apparatus 10 and the portable X-ray source 70 (plural diagnostic device).

What is claimed is:

1. A diagnostic device system comprising:
   a diagnostic device that is supplied with electric power for operation and is used for diagnosing diseases of humans or animals;
   a rechargeable battery for operation that is charged by a rechargeable battery for charging, wherein the rechargeable battery for charging is mounted on a vehicle and is used to charge the rechargeable battery for operation and to realize the functions of the vehicle and the rechargeable battery for operation supplies electric power to the diagnostic device to operate the diagnostic device; and
   an accommodating unit that houses the rechargeable battery for operation therein and corn rises an electric cable for supplying electric power from the housed rechargeable battery for operation to the diagnostic device.

2. The diagnostic device system of claim 1, wherein the diagnostic device is at least one of a portable radiographic apparatus for recording a radiological image expressed by irradiated radiation or a portable X-ray source for irradiating radiation on the portable radiographic apparatus.

3. The diagnostic device system of claim 1, wherein the vehicle on which the rechargeable battery for charging is mounted is an automobile.

4. The diagnostic device system of claim 2, wherein the vehicle on which the rechargeable battery for charging is mounted is an automobile and the rechargeable battery for charging is used to realize the functions of the automobile.

5. The diagnostic device system of claim 1, wherein the capacity of the rechargeable battery for operation is smaller than the capacity of the rechargeable battery for charging.

6. The diagnostic device system of claim 1, wherein the rechargeable battery for operation has a larger self-discharging rate than the rechargeable battery for charging.

7. The diagnostic device system of claim 1, wherein the rechargeable battery for operation is attachable to and detachable from the diagnostic device.

* * * * *